United States Patent
Kim et al.

(10) Patent No.: US 11,254,925 B2
(45) Date of Patent: Feb. 22, 2022

(54) ENZYME-POROUS CARBON COMPOSITE

(71) Applicant: Korea University Research and Business Foundation, Seoul (KR)

(72) Inventors: Jungbae Kim, Seoul (KR); Young Jun Ju, Seoul (KR); Li Na Kim, Seoul (KR); Ja Hyun Nam, Seoul (KR); In Seon Lee, Yongin-si (KR)

(73) Assignee: Korea University Research and Business Foundation, Seoul (KR)

(*) Notice: Subject to any disclaimer, the term of this patent is extended or adjusted under 35 U.S.C. 154(b) by 0 days.

(21) Appl. No.: 17/118,814

(22) Filed: Dec. 11, 2020

(65) Prior Publication Data

US 2021/0115431 A1 Apr. 22, 2021

Related U.S. Application Data

(63) Continuation of application No. PCT/KR2019/016745, filed on Nov. 29, 2019.

(30) Foreign Application Priority Data

Jan. 31, 2019 (KR) .................. 10-2019-0012428

(51) Int. Cl.
*C12N 11/14* (2006.01)
*C12N 9/96* (2006.01)

(52) U.S. Cl.
CPC ............... *C12N 11/14* (2013.01); *C12N 9/96* (2013.01)

(58) Field of Classification Search
None
See application file for complete search history.

(56) References Cited

U.S. PATENT DOCUMENTS

| 4,438,196 A * | 3/1984 | Lantero, Jr. ............ C12N 11/14 |
| | | 435/96 |
| 5,380,422 A * | 1/1995 | Negishi .............. G01N 27/4035 |
| | | 204/294 |
| 9,356,297 B1 | 5/2016 | Atanassov et al. |
| 10,141,577 B2 * | 11/2018 | Kim .................... H01M 8/0241 |

FOREIGN PATENT DOCUMENTS

| CN | 105836731 A | 8/2016 |
| CN | 107760668 A | 3/2018 |
| KR | 10-1995-0008685 A | 4/1995 |
| KR | 10-2005-0062989 A | 6/2005 |
| KR | 10-2013-0124194 A | 11/2013 |
| KR | 10-2016-0092652 A | 8/2016 |
| KR | 10-2018-0041065 A | 4/2018 |

OTHER PUBLICATIONS

Byoung Chan Kim, et al., "Fabrication of enzyme-based coatings on intact multi-walled carbon nanotubes as highly effective electrodes in biofuel cells", Scientific Reports, Jan. 5, 2017, pp. 1-10.
International Search Report for PCT/KR2019/016745 dated Mar. 24, 2020 (PCT/ISA/210).

* cited by examiner

*Primary Examiner* — Anand U Desai
(74) *Attorney, Agent, or Firm* — Sughrue Mion, PLLC

(57) ABSTRACT

The present invention relates to an enzyme-porous carbon composite, and more specifically, to an enzyme-porous material composite capable of realizing a much higher enzyme adsorption amount than porous silica and maintaining high stability of an immobilized enzyme.

12 Claims, 11 Drawing Sheets

FIG. 11B

ENZYME-POROUS CARBON COMPOSITE

CROSS REFERENCE TO RELATED APPLICATIONS

This application is a continuation application of, and claims priority from International Application No. PCT/KR2019/016745 filed Nov. 29, 2019, claiming priority from Korean Patent Application No. 10-2019-0012428 filed Jan. 31, 2019, the entire disclosures of which are incorporated herein by reference.

TECHNICAL FIELD

The present invention relates to an enzyme-porous carbon composite, and more specifically, to an enzyme-porous carbon composite in which an enzyme is effectively immobilized in a porous carbon material by preventing enzyme leakage for a long time as a technique of improving the stability of an enzyme by immobilizing an enzyme in a porous material.

BACKGROUND ART

Enzymes are biocatalysts that promote various chemical reactions and can be used in various industries because the enzymes have high selectivity, precision, and efficiency and promote chemical reactions at very high rates even at room temperature and atmospheric pressure. However, in an industrial reaction environment, the three-dimensional structure of the enzymes is easily denatured due to external environments such as heat, pH, shear stress, and the like, and thus, the enzymes rapidly lose their activity. Therefore, various studies have been conducted to improve the stability of enzymes.

Among techniques of improving the stability of an enzyme, the technique of immobilizing an enzyme on a solid support not only improves the stability of the enzyme but also allows the immobilized enzyme to be easily separated from a reaction solution as a heterogeneous catalyst. In particular, porous materials are being researched as optimal materials for immobilization of an enzyme because it is possible to variously adjust the size and shape of pores of the porous materials in response to the size of enzyme. In addition, when the enzyme is immobilized in the porous material, the stability of the enzyme can be significantly improved due to a crowding effect in which the enzyme is present at a high concentration of several hundred milligrams per unit milliliter in the pores of the porous material. Also, since the porous material can protect the enzyme immobilized therein from physical impact such as external shear stress and the like, an enzymatic reaction can be achieved even in harsh environments.

However, the enzyme loaded in a general porous material may easily leak to the outside, and the leaked enzyme may not be recovered but discarded, or the enzyme structure may be denatured by the external environment, resulting in a decrease in activity of the immobilized enzyme.

To solve these problems, a technique of preventing enzyme leakage by covalently bonding an enzyme to the inside of a porous material was studied. This technique is for preventing the leakage of the enzyme loaded in the porous material by functionalizing the porous material using a physicochemical method and then forming a crosslink between a functional group of the porous material and a functional group of an enzyme side chain using a crosslinking agent.

However, in order to apply the covalent bonding technique, an additional functionalization process needs to be introduced in the process of synthesizing the porous material. In addition, when two or more covalent bonds are induced between a functional group on the inner surface of the pore of the porous material and a functional group on the enzyme surface, the enzyme may be structurally denatured and thus deactivated.

Meanwhile, a nanoscale enzyme reactor technique that applies the covalent bonding technique was studied to prevent the leakage of an enzyme. The nanoscale enzyme reactor technique is a technique of preventing the leakage of the enzyme loaded in a porous material by loading the enzyme in a porous material and forming a crosslink between loaded enzyme molecules before the enzyme leaks to increase the size of crosslinked enzyme molecules compared to the inlet diameter of the pore of the porous material.

However, in the case of the conventional nanoscale enzyme reactor technique, two or more crosslinks may be induced on the enzyme surface by a crosslinking agent, and it is difficult for this technique to stabilize unstable enzymes such as formate dehydrogenase, formaldehyde dehydrogenase, alcohol dehydrogenase, and the like, which are easily denatured and thus deactivated.

In addition, when the enzymes are stabilized using a crosslinking agent, there may be a problem of biocompatibility of the crosslinking agent such as glutardialdehyde or the like, and therefore, it is difficult to utilize this technique in the medical field.

DISCLOSURE

Technical Problem

The present invention is directed to providing an enzyme-porous carbon composite in which an enzyme is immobilized in a porous material while minimizing a decrease in enzyme activity, so that the enzyme immobilized in the porous material is prevented from leaking, and the stability of the enzyme immobilized in the porous material is ensured.

[The National R&D Project of Korea supports the present invention]
Assignment No: 20182010600430
Department name: Ministry of Trade, Industry and Energy
Research management agency: Korea Institute of Energy Technology Evaluation and Planning
Research project name: Energy Technology Development Project
Research title: Development of $CO_2$ conversion process technology based on highly integrated and highly stable enzyme system
Supervising organization: Korea University
Research period: 2019.04.01~2019.12.31

Technical Solution

One aspect of the present invention provides an enzyme-porous carbon composite which includes a porous carbon carrier and an enzyme loaded in a pore of the porous carbon carrier.

According to an embodiment of the present invention, the enzyme may be loaded by molecules thereof being at least partially adsorbed onto the inside of the pore of the porous carbon carrier.

In addition, the porous carbon carrier may be mesoporous carbon and/or microporous carbon and may, for example, have a pore size of 1 to 5,000 nm. In addition, the enzyme may include one or more enzymes selected from the group consisting of trypsin, chymotrypsin, pepsin, a lipase, glucose oxidase, horseradish peroxidase, tyrosinase, carbonic anhydrase, formaldehyde dehydrogenase, formate dehydrogenase, alcohol dehydrogenase, cholesterol dehydrogenase, acylase, lactonase, a protease, a peroxidase, an aminopeptidase, a phosphatase, a transaminase, serine endopeptidase, cysteine endopeptidase, and a metalloendopeptidase.

In addition, the porous carbon carrier may further include a first functional group on a surface of the pore thereof to induce one or more of a hydrophobic interaction and a hydrophilic interaction with the enzyme.

In addition, the first functional group may include at least one of one or more hydrophobic interaction-inducing functional groups selected from the group consisting of an alkyl group, a phenyl group, a benzyl group, a vinyl group, and a halo group and one or more hydrophilic interaction-inducing functional groups selected from the group consisting of a hydroxy group, a carbonyl group, a halide group, a carboxyl group, a methoxy group, a hydroperoxy group, an amine group, an imine group, an imide group, a nitrile group, a nitro group, a thiol group, a sulfino group, and a phosphate group.

In addition, the enzyme may further include a second functional group to induce one or more of a hydrophobic interaction and a hydrophilic interaction with a pore surface of the porous carbon carrier.

In addition, the second functional group may include at least one of one or more hydrophobic interaction-inducing functional groups selected from the group consisting of an alkyl group, a phenyl group, a benzyl group, a vinyl group, and a halo group and one or more hydrophilic interaction-inducing functional groups selected from the group consisting of a hydroxy group, a carbonyl group, a halide group, a carboxyl group, a methoxy group, a hydroperoxy group, an amine group, an imine group, an imide group, a nitrile group, a nitro group, a thiol group, a sulfino group, and a phosphate group.

In addition, the enzyme-porous carbon composite may exhibit an enzyme release amount of less than 33% compared to before stirring, as measured after being stirred in a mixed state with a buffer solution for 12 days.

In addition, the enzyme-porous carbon composite may exhibit an enzyme activity of 16% or more compared to before stirring, as measured after being stirred in a mixed state with a buffer solution for 12 days.

In addition, the enzyme-porous carbon composite may exhibit an enzyme activity of 72% or more compared to before stirring, as measured after being stirred in a mixed state with a buffer solution for 45 days.

Another aspect of the present invention provides an electrode for a biofuel cell or a biosensor which includes the enzyme-porous carbon composite according to the present invention.

Still another aspect of the present invention provides a carbon dioxide conversion system which includes the enzyme-porous carbon composite according to the present invention.

Yet another aspect of the present invention provides an anti-fouling system which includes the enzyme-porous carbon composite according to the present invention.

Advantageous Effects

An enzyme-porous carbon composite according to the present invention can be suitably used to immobilize an enzyme in porous carbon without denaturation of an active site of the enzyme and stabilize the enzyme. In addition, the composite can be used in the medical field where the use thereof is limited by immobilizing and stabilizing the enzyme without using a component having a problem of biocompatibility, such as a crosslinking agent applied to a conventional enzyme stabilization technique. Additionally, when the enzyme-porous carbon composite is utilized to immobilize enzymes such as glucose oxidase and the like for the purpose of producing electrodes for glucose-based biofuel cells and biosensors for measuring blood glucose, a very high stabilization effect can be achieved. In addition, when the enzyme-porous carbon composite is utilized to immobilize enzymes such as carbonic anhydrase capable of converting carbon dioxide into bicarbonate, formate dehydrogenase capable of converting bicarbonate into formic acid, and the like, it is possible to stably maintain the activity of the enzymes for a long time compared to a conventional immobilization method using a porous material, and thus it can be used as a catalyst material for a carbon dioxide conversion and utilization system. Additionally, when the enzyme-porous carbon composite is utilized to immobilize an enzyme such as acylase which is capable of suppressing biofilm formation by decomposing a signaling molecule that plays a role in quorum sensing, it is possible to stably maintain the activity of the enzyme compared to the conventional immobilization method using a porous material, and thus it can be used as a catalyst material in an anti-fouling system for the purpose of suppressing biofilm formation on a membrane surface.

MODES OF THE INVENTION

Hereinafter, the present invention will be described in detail with reference to the appended drawings so that those skilled in the art can easily carry out the present invention. However, the present invention may be embodied in several different forms, and therefore, is not limited to embodiments described herein.

Figure 1:
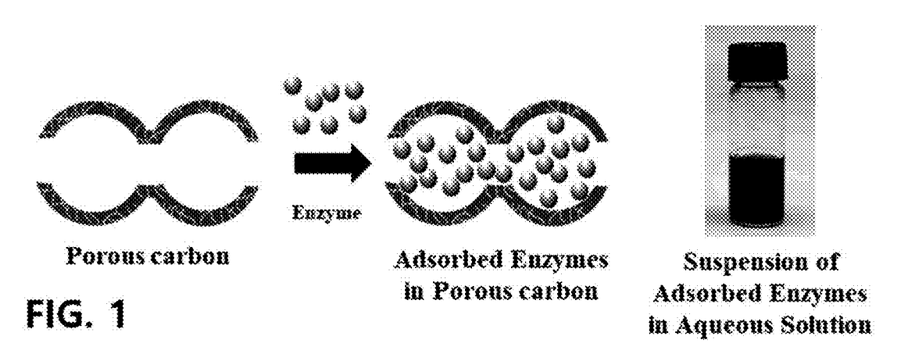
FIG. 1 is a schematic diagram illustrating a process of manufacturing an enzyme-porous carbon composite according to an embodiment of the present invention.

Referring to FIG. 1, an enzyme-porous carbon composite according to an embodiment of the present invention is implemented by including an enzyme and a porous carbon carrier, and specifically, the enzyme is loaded in a pore provided in the porous carbon carrier. In this case, the enzyme may be loaded in the pore without forming a covalent bond between the pore surface of the porous carbon carrier and the enzyme or between enzyme molecules. As an example, the enzymes may be provided while being adsorbed onto the pore of the porous carbon carrier. In this case, at least some of the plurality of enzymes in the adsorbed state may be adsorbed onto the surface of the pore of the porous carbon carrier. In addition, the enzymes may be provided in the pore while being adsorbed onto any one enzyme and another adjacent enzyme. In this case, as enzyme molecules are agglomerated without forming a covalent bond between the enzyme molecules, the formed agglomerate may have a relatively larger physical size compared to the inlet diameter of the pore, thereby minimizing or preventing the leakage of the enzyme from the pore.

Meanwhile, even when the enzyme is loaded in the pore of the porous material, the enzyme may not be prevented from leaking by the adsorption between the pore surface of the porous material and the enzyme or adsorption between the enzyme molecules as described above. In addition, regardless of the type of porous material, the enzyme may not be introduced into the pore of the porous material in an amount corresponding to the volume of the pore.

The present inventor has found that when a porous carbon material is used as a carrier instead of porous silica often conventionally used to carry an enzyme in a pore inside a porous material, a large amount of enzyme may be loaded in the pore, and the activity of the loaded enzyme may be stably maintained for a long time. Therefore, the present invention has been completed based on these facts. This effect may be evaluated as a breakthrough that could not be expected with conventional enzyme immobilization and stabilization methods which have to use a crosslinking agent to prevent the leakage of the enzyme loaded in the porous material or to have a functional group for forming a covalent bond.

Figure 2:
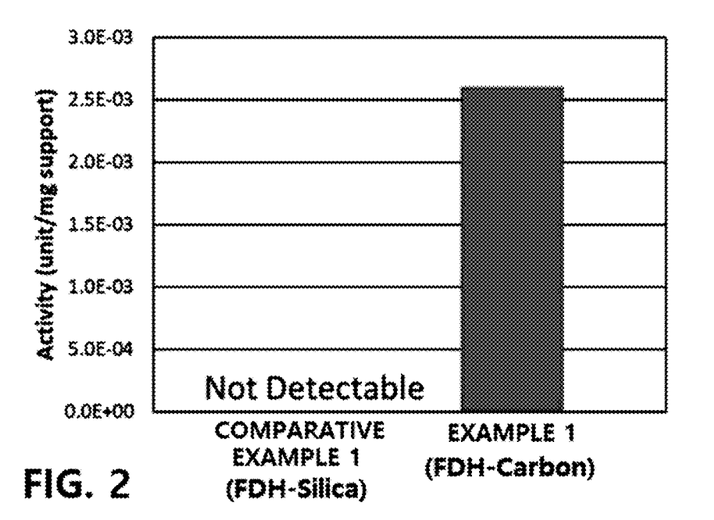
FIG. 2 a graph illustrating the enzyme activity per unit weight of porous carbon in a formate dehydrogenase-porous carbon composite according to an embodiment of the present invention.
Figure 3A:
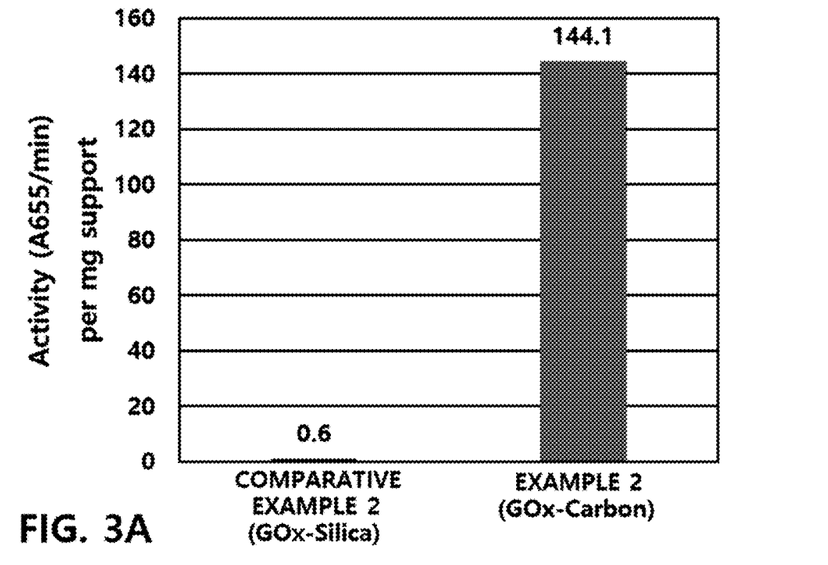
FIGS. 3A to 3C are graphs illustrating the enzyme activity per unit weight of porous carbon in a glucose oxidase-porous carbon composite, a carbonic anhydrase-porous carbon composite, and an acylase-porous carbon composite according to an embodiment of the present invention, respectively.
Figure 3B:
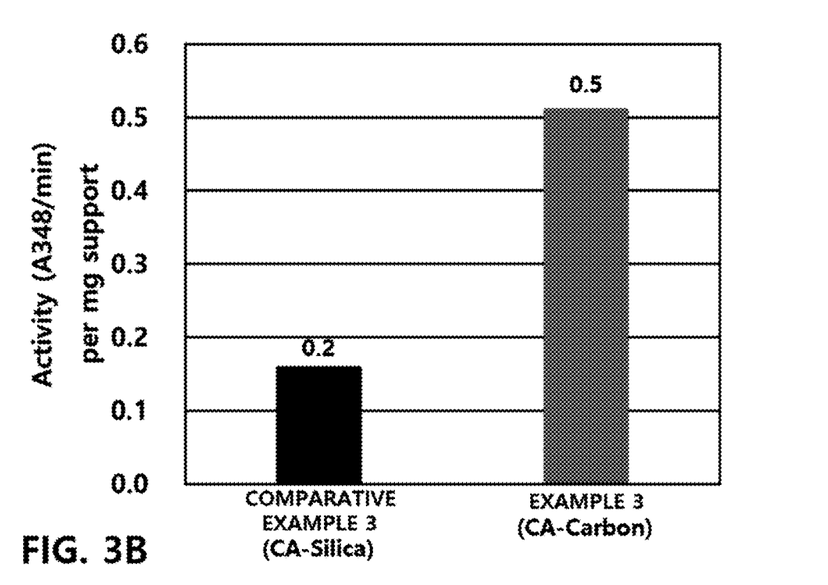
Figure 3C:
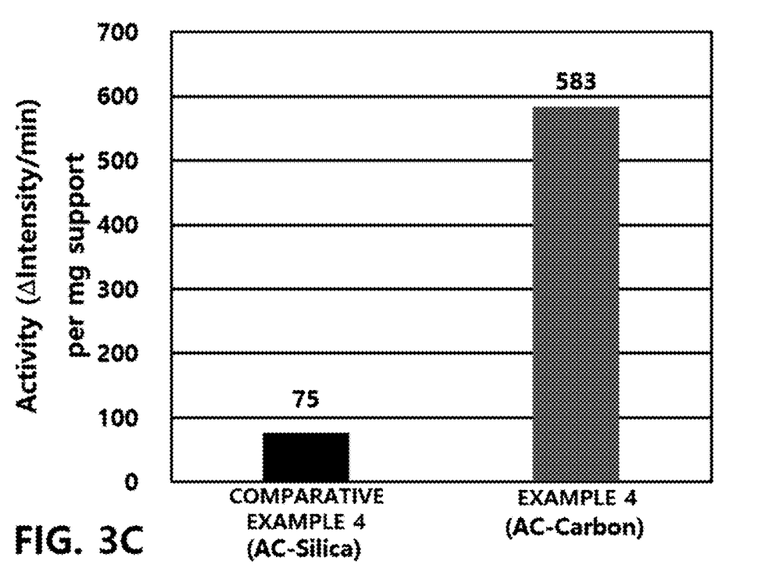

That is, as shown in FIG. 2, in the case of Comparative Example 1 in which silica is used as a porous material, even though formate dehydrogenase (FDH) is loaded, the activity of the FDH enzyme could not be measured. On the other hand, in the case of Example 1 in which porous carbon is used as a porous material, even though the treatment with the same enzyme is performed in the same manner, remarkably excellent enzyme activity is detected. These technical features are confirmed as in experiments in which the type of enzyme is changed to glucose oxidase (GOx), carbonic anhydrase (bCA), and acylase (AC) as shown in FIGS. 3A to 3C, and enzyme activity is measured even when porous silica is used (Comparative Examples 2 to 4), but the degree thereof is significantly lower than that when porous carbon is used (Examples 2 to 4).

Figure 4:
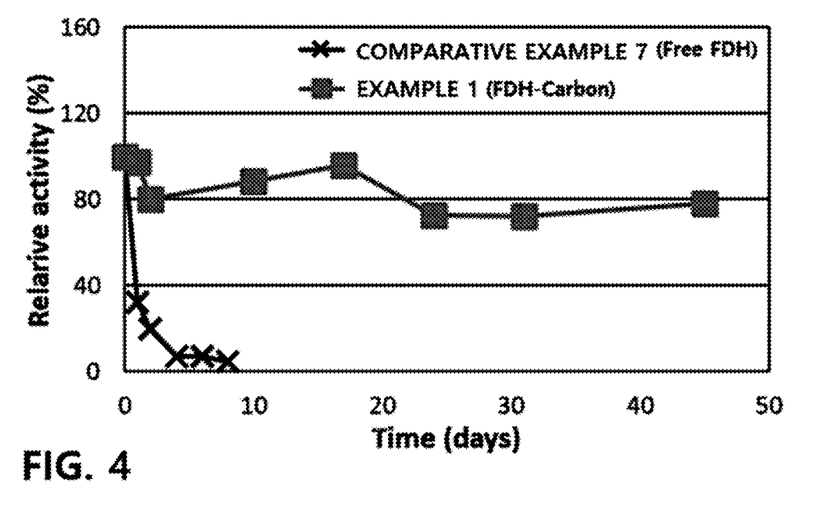
FIG. 4 is a graph of measuring the stability of enzyme activity of a formate dehydrogenase-porous carbon composite according to an embodiment of the present invention over time.
Figure 5A:
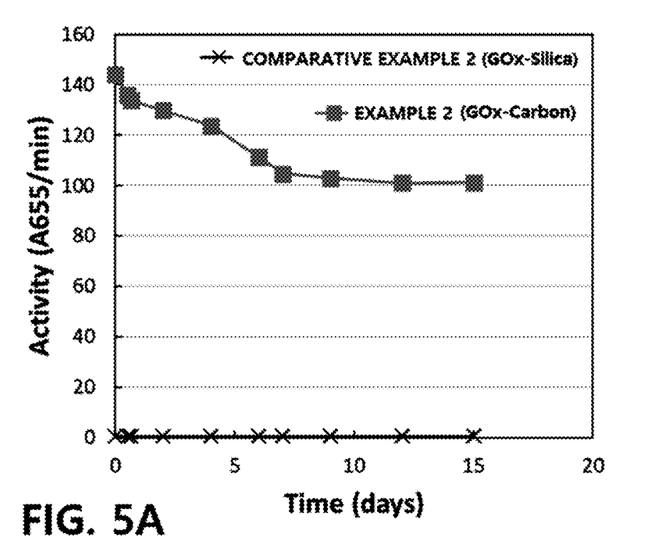
FIGS. 5A to 5C are graphs of measuring the stability of enzyme activity of a glucose oxidase-porous carbon composite, a carbonic anhydrase-porous carbon composite, and an acylase-porous carbon composite according to an embodiment of the present invention over time, respectively.
Figure 5B:
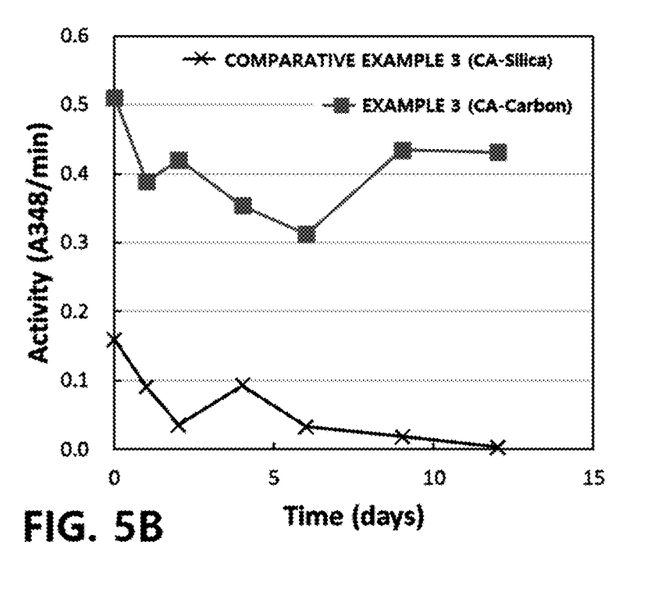
Figure 5C:
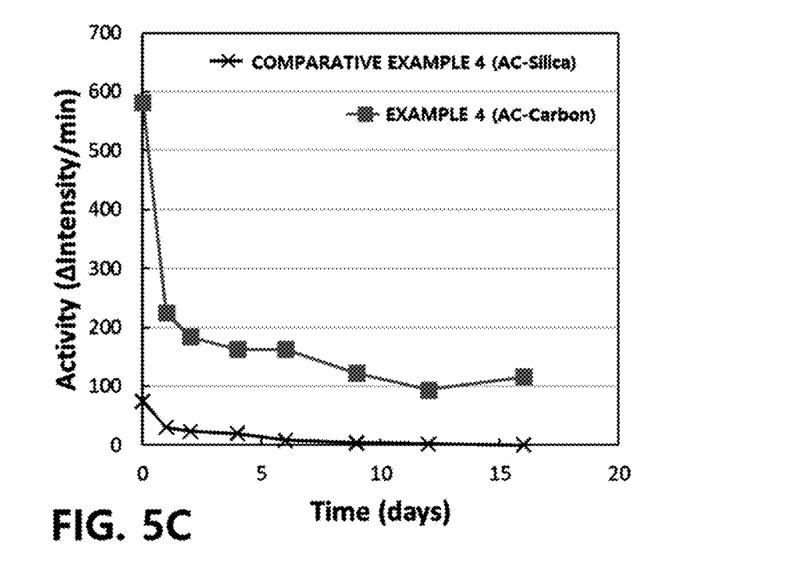

In addition, as shown in FIG. 4, in the case of Comparative Example 7 in which a free enzyme is provided in a solution instead of Comparative Example 1 in which activity could not be measured, enzyme activity is rapidly lowered to less than 40% compared to the initial activity one day before and then almost disappears within 2 to 3 days. However, the activity of the enzyme loaded in the pore of the porous carbon lasts 45 days or more while maintaining a level close to 80% compared to the initial activity. These technical features are confirmed as in experiments in which the type of enzyme is changed to glucose oxidase, carbonic anhydrase, and acylase as shown in FIGS. 5A to 5C. In conclusion, the enzyme-porous carbon composite according to the embodiment of the present invention may stably exhibit enzyme activity for a long time while preventing the leakage of the enzyme in the porous carbon without any covalent bonds.

Figure 6A:
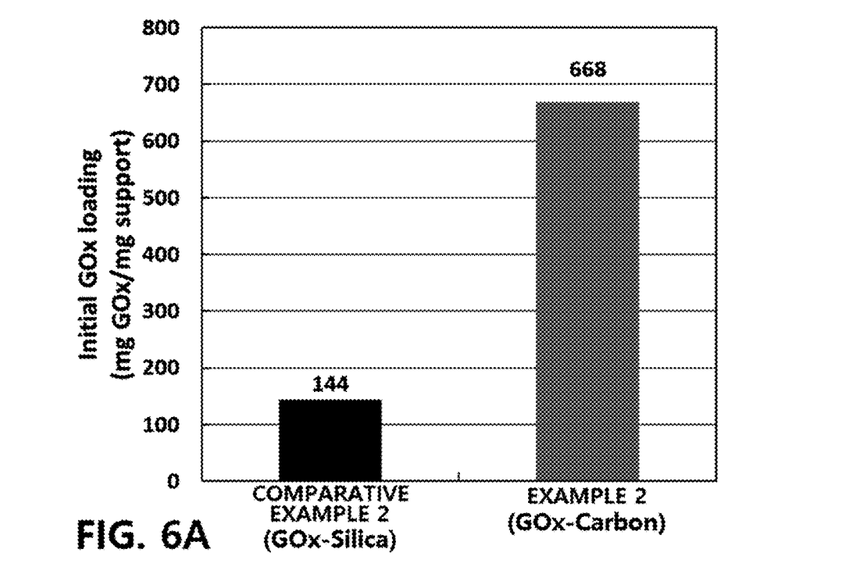
FIGS. 6A to 6C are graphs illustrating the initial enzyme loading amount per unit weight of porous carbon in a glucose oxidase-porous carbon composite, a carbonic anhydrase-porous carbon composite, and an acylase-porous carbon composite according to an embodiment of the present invention, respectively.
Figure 6B:
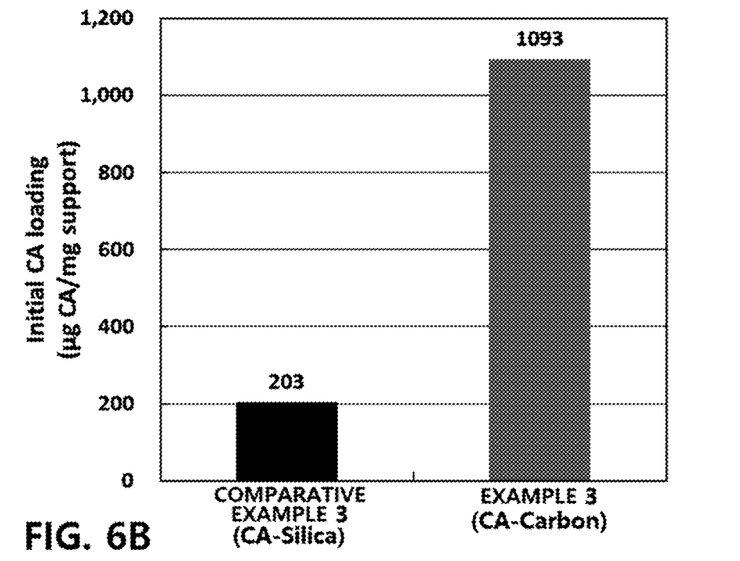
Figure 6C:
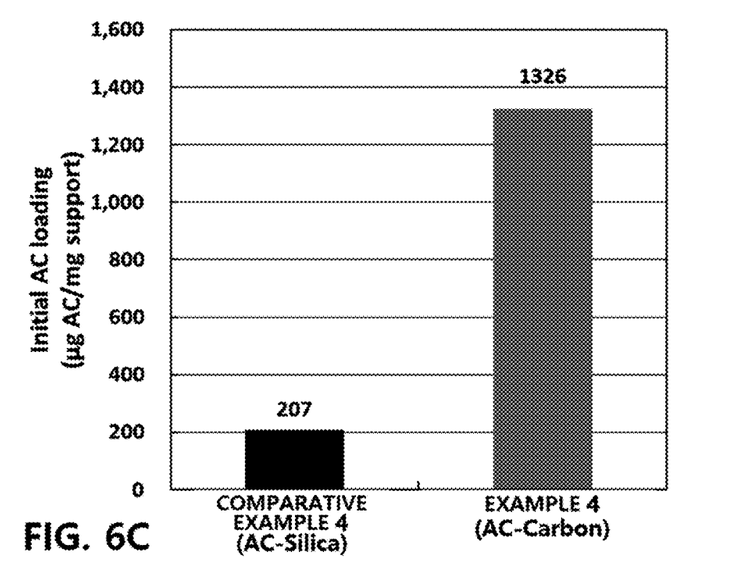
Figure 7A:
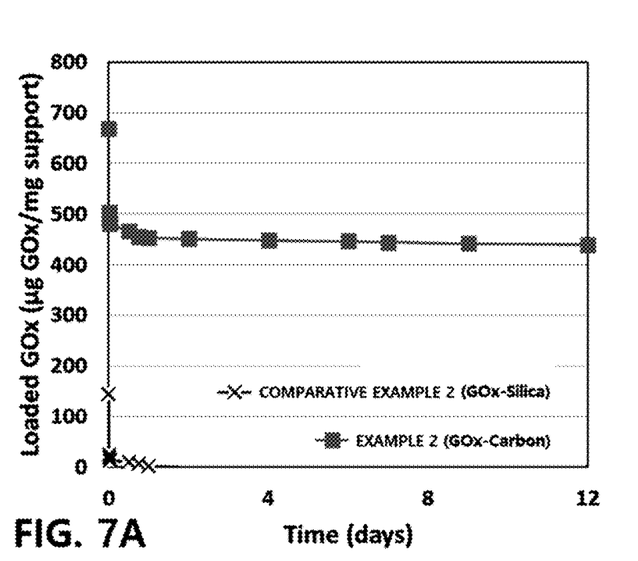
FIGS. 7A to 7C are graphs illustrating a change in enzyme loading amount per unit weight of porous carbon in a glucose oxidase-porous carbon composite, a carbonic anhydrase-porous carbon composite, and an acylase-porous carbon composite according to an embodiment of the present invention over storage time, respectively.
Figure 7B:
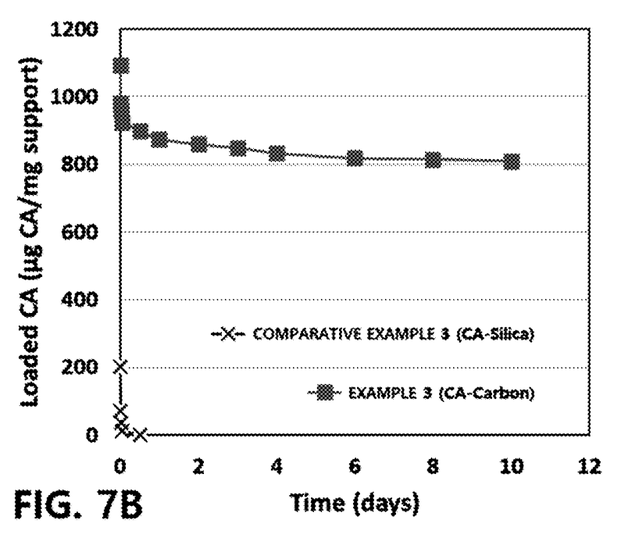
Figure 7C:
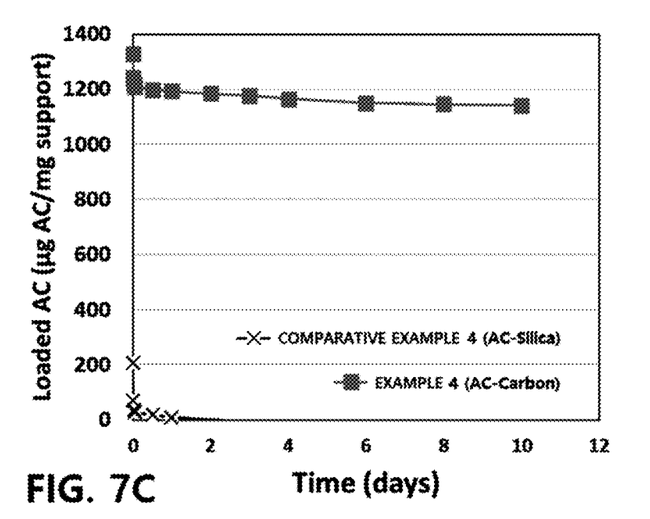

In addition, referring to FIGS. 6A to 6C, Examples 2 to 4 in which carbon is used as a porous carrier exhibit significantly higher enzyme (glucose oxidase, carbonic anhydrase, and acylase) loading amounts as compared to Comparative Examples 2 to 4 in which silica is used as a porous carrier. Also, as shown in FIGS. 7A to 7C, the enzyme molecules loaded in the porous carbon remain almost unleaked after one day has elapsed. Therefore, the porous carbon carrier has advantages in which the enzyme may be easily introduced into the pore thereof compared with other porous materials, a larger amount of enzyme may be loaded compared to when a silica carrier is used, and the enzyme may be stably loaded by preventing the leakage of the enzyme even when a stirring reaction is continuously performed after introduction. The porous carbon carrier may be used without limitation as long as it is a carbon material having a plurality of pores therein, preferably, a carbon material capable of interacting with the enzyme. As one example, the porous carbon may be porous carbon having a pore size of 1 to 5,000 nm, as another example, 1 to 1,000 nm, and as still another example, 1 to 500 nm, but the present invention is not limited thereto.

In addition, although not limited in a shape thereof, the porous carbon carrier may be, for example, a spherical shape, an elliptical shape, or an amorphous particle or implemented in the form of a film on the surface. Also, the particle-type porous carbon carrier may have a size of 100 nm to 1,000 μm, and in this case, the size of the carrier means a diameter in the case of a spherical shape and a maximum distance between two different points on a surface in the case of an amorphous shape.

In addition, the porous carbon carrier may have a surface area of 100 to 5,000 $m^2/g$ and a pore volume of 0.1 to 10 $cm^3/g$, but the present invention is not limited thereto.

According to the embodiment of the present invention, the porous carbon carrier may further include a first functional group capable of inducing an interaction with the enzyme to prevent the leakage of the loaded enzyme and stably exhibit enzyme activity for a long time, and specifically, the functional group may be provided at least on the surface of the pore in the porous carbon carrier. The interaction is a noncovalent interaction and may be, for example, a hydrophobic interaction or a hydrophilic interaction. The hydrophilic interaction may be, for example, a hydrogen bond or an ionic bond. Since the interaction minimizes or prevents the conformation of the enzyme from being affected compared with a covalent bond, it is possible to prevent or minimize the conventional problems of the conformational modification of the enzyme, which is caused by a strong binding force that is generated when the enzyme is immobilized in the support by a covalent bond or a crosslink between enzyme molecules is formed by a covalent bond, and the resulting degradation or loss of enzyme activity. In this case, as the first functional group included in the porous carbon carrier, a functional group capable of inducing a hydrophobic interaction may be advantageous for introducing the enzyme into the pore, preventing the leakage of the enzyme, and stably immobilizing the enzyme for a long time rather than a functional group capable of inducing a hydrophilic interaction. However, it should be noted that depending on characteristics of the enzyme to be introduced, a functional group capable of inducing a hydrophilic interaction may sometimes be advantageous.

The first functional group may be used without limitation as long as it is a functional group capable of inducing a hydrophobic interaction or a hydrophilic interaction and may, for example, include at least one of one or more hydrophobic interaction-inducing functional groups selected from the group consisting of an alkyl group, a phenyl group, a benzyl group, a vinyl group, and a halo group and one or more hydrophilic interaction-inducing functional groups selected from the group consisting of a hydroxy group, a carbonyl group, a halide group, a carboxyl group, a methoxy group, a hydroperoxy group, an amine group, an imine group, an imide group, a nitrile group, a nitro group, a thiol group, a sulfino group, and a phosphate group.

In addition, the first functional group may be introduced onto the pore surface of the porous carbon by known methods, but the present invention is not particularly limited thereto.

Figure 8:
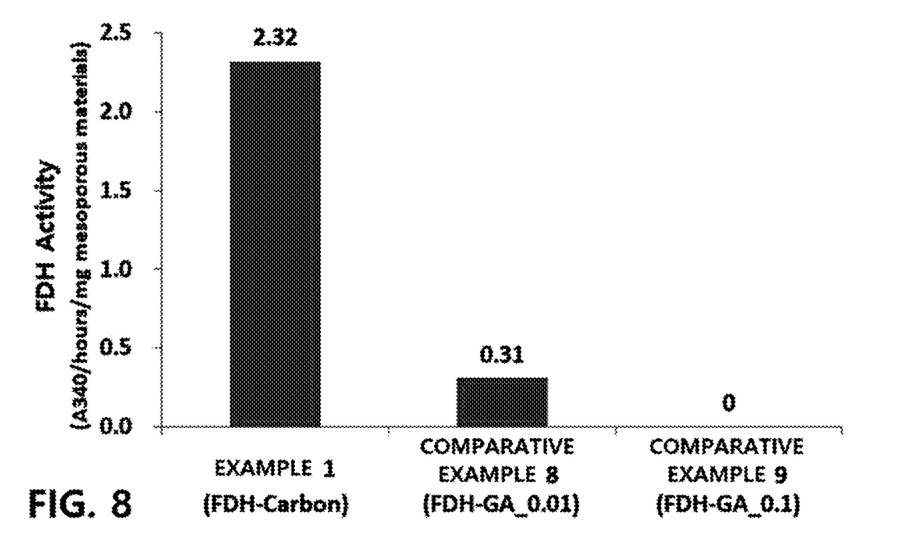
FIG. 8 is a graph of comparing the activities of a formate dehydrogenase-porous carbon composite according to an embodiment of the present invention and composites in which crosslinked formate dehydrogenase is immobilized in porous carbon.
Figure 9A:
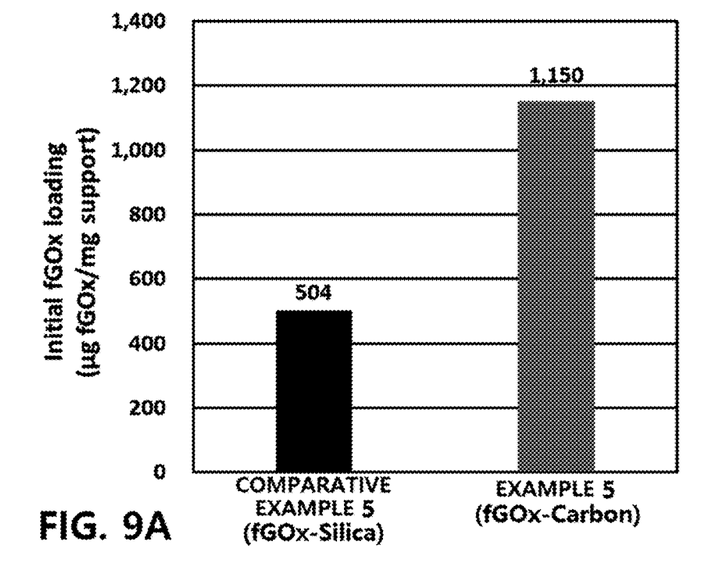
FIGS. 9A and 9B are graphs illustrating the initial enzyme loading amount per unit weight of porous carbon in a glucose oxidase-porous carbon composite and an acylase-porous carbon composite which are treated with functional groups according to an embodiment of the present invention, respectively.
Figure 9B:
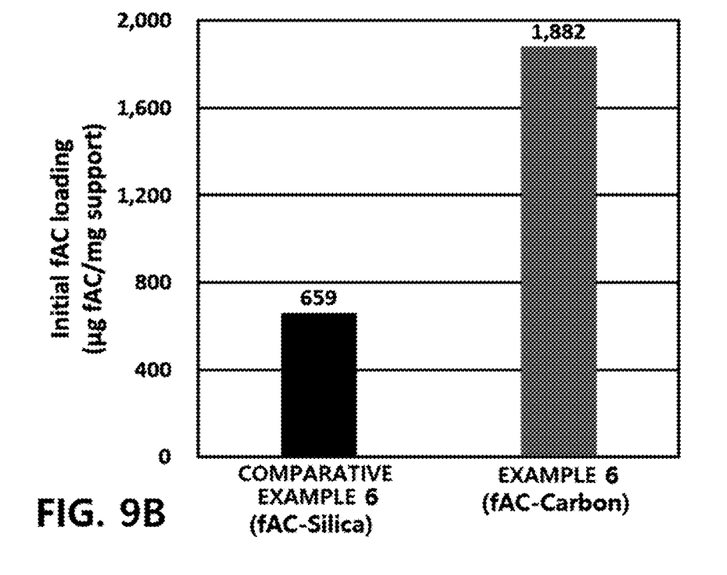

Next, the enzyme loaded in the pore of the above-described porous carbon carrier may be used without limitation as long as it is a known enzyme. Preferably, the enzyme may include one or more selected from the group consisting of trypsin, chymotrypsin, pepsin, a lipase, glucose oxidase, horseradish peroxidase, tyrosinase, carbonic anhydrase, formaldehyde dehydrogenase, formate dehydrogenase, alcohol dehydrogenase, cholesterol dehydrogenase, acylase, lactonase, a protease, a peroxidase, an aminopeptidase, a phosphatase, a transaminase, serine endopeptidase, cysteine endopeptidase, and a metalloendopeptidase. In particular, one or more enzymes selected from the group consisting of formate dehydrogenase, formaldehyde dehydrogenase, alcohol dehydrogenase, and the like, whose activity may be degraded when the enzymes are immobilized by a covalent bond or a crosslink due to somewhat low stability of the conformation, may stably exhibit their activity when loaded in the porous carbon carrier according to the present invention. Referring to FIG. 8, unlike Example 1 including formate dehydrogenase adsorbed onto the inside of the porous carrier, in the case of Comparative Examples 8 and 9 in which formate dehydrogenase crosslinked by a crosslinking agent is included in a solution in the porous carrier, enzyme activity is dramatically degraded as the concentration of the crosslinking agent increases. In conclusion, the enzyme-porous carbon composite according to the embodiment of the present invention may stably exhibit enzyme activity when the enzyme is loaded in the porous carbon carrier.

According to the embodiment of the present invention, the enzyme may further include a second functional group to induce a noncovalent interaction, specifically, one or more of a hydrophobic interaction and a hydrophilic interaction for the purpose of enhancing an interaction between the enzyme and the porous carbon carrier and/or the enzyme molecules loaded in the pore of the carrier. The second functional group may function to prevent the leakage of the enzyme from the pore of the porous carbon while minimizing the effect on the conformation of the enzyme and stably exhibit enzyme activity. The second functional group may be used without limitation as long as it is a functional group capable of inducing a hydrophobic interaction or a hydrophilic interaction and may, for example, include at least one of one or more hydrophobic interaction-inducing functional groups selected from the group consisting of an alkyl group, a phenyl group, a benzyl group, a vinyl group, and a halo group and one or more hydrophilic interaction-inducing functional groups selected from the group consisting of a hydroxy group, a carbonyl group, a halide group, a carboxyl group, a methoxy group, a hydroperoxy group, an amine group, an imine group, an imide group, a nitrile group, a nitro group, a thiol group, a sulfino group, and a phosphate group.

When describing and referring to FIGS. 9A to 11B relating to a loading amount according to interaction by the second functional group introduced into the enzyme and the stabilization of the enzyme, it may be confirmed that glucose oxidase in which a vinyl group is introduced onto the surface thereof using acryloyl chloride and acylase in which a vinyl group is introduced onto the surface thereof in the same manner are loaded in a significantly improved amount as compared to that of a composite formed of an enzyme not including the second functional group and a porous carbon carrier. Meanwhile, when porous silica is used as a porous carrier, even though a second functional group capable of inducing an interaction is included in an enzyme, a significantly smaller amount of the enzyme is loaded as compared to that when an enzyme not including a second functional group is loaded in a porous carbon carrier.

Figure 10A:
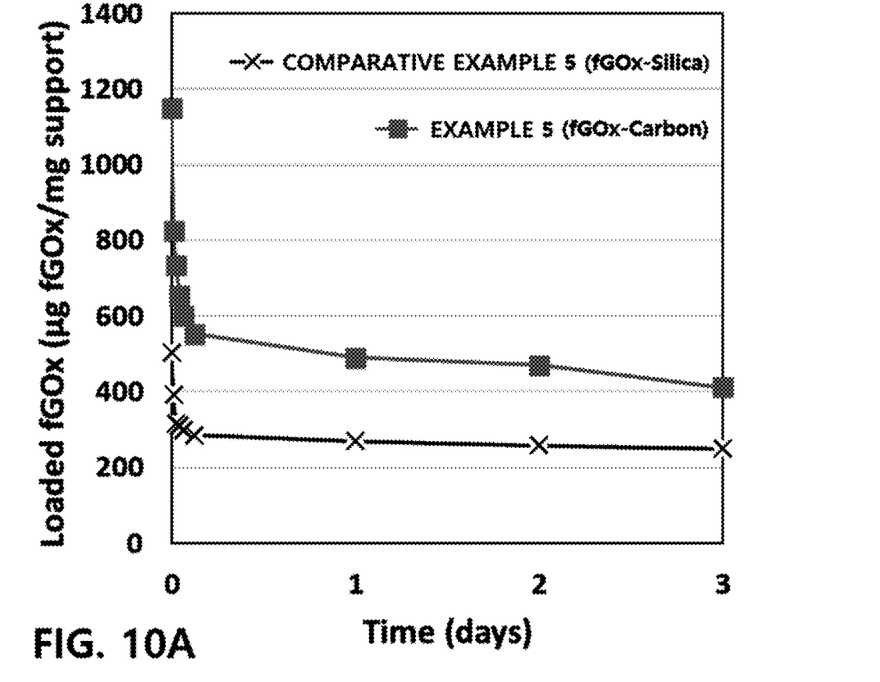
FIGS. 10A and 10B are graphs illustrating a change in enzyme loading amount per unit weight of porous carbon in a glucose oxidase-porous carbon composite and an acylase-porous carbon composite which are treated with functional groups according to an embodiment of the present invention over storage time, respectively.
Figure 10B:
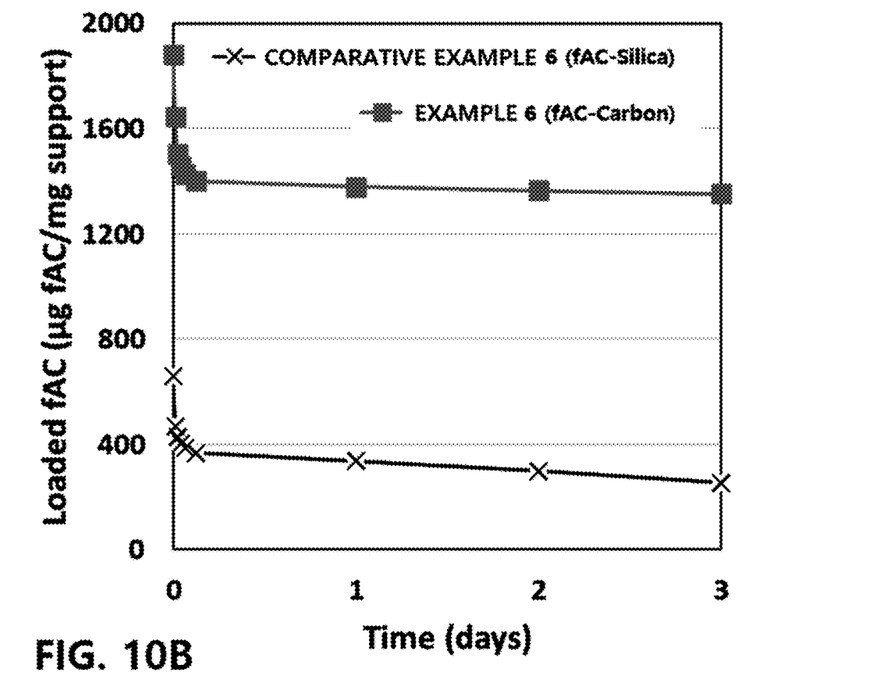
Figure 11A:
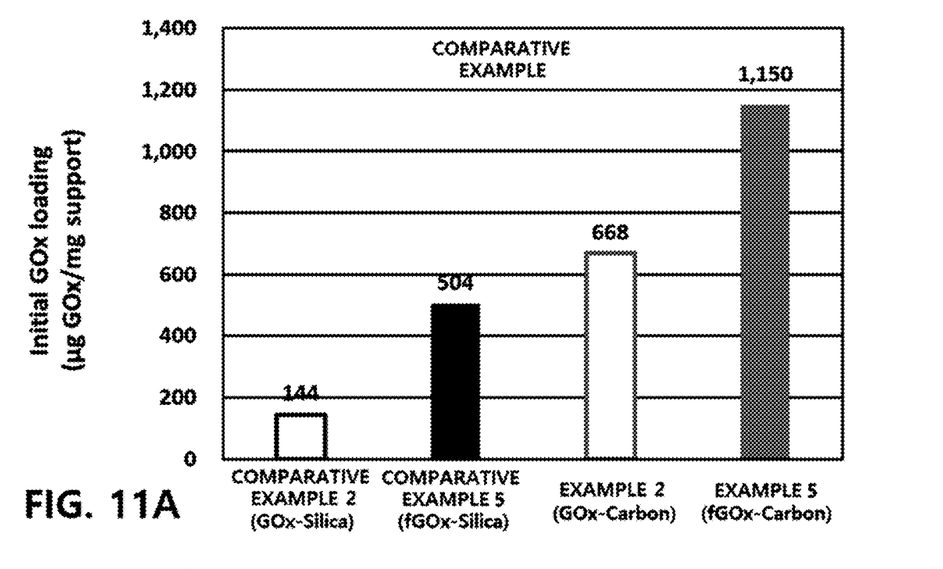
FIGS. 11A and 11B are graphs illustrating the initial enzyme loading amount per unit weight of porous carrier in a glucose oxidase-porous carbon composite, an acylase-porous carbon composite, a functional group-treated glucose oxidase-porous carbon composite, a functional group-treated acylase-porous carbon composite, and composites implemented by changing a porous carrier to porous silica according to an embodiment of the present invention.
Figure 11B:
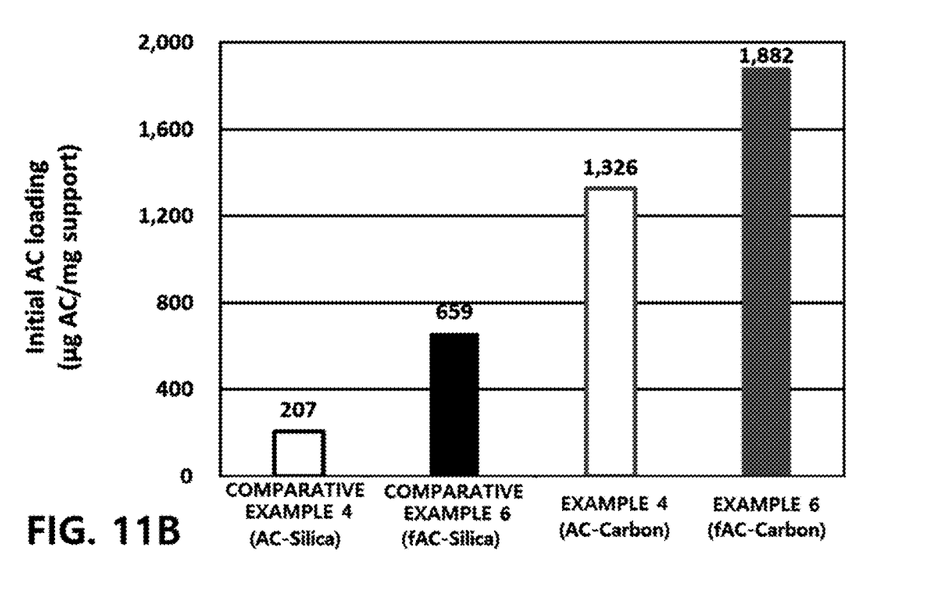

When describing and referring to FIG. 10 relating to an amount of the enzyme leaked after loading, it was confirmed that the enzyme molecules loaded in the porous carbon remain almost unleaked after one day had elapsed.

In conclusion, the porous carbon carrier has advantages in which the enzyme may be easily introduced into the pore thereof compared with other porous materials, a larger amount of enzyme may be loaded compared to when a silica carrier is used, and the enzyme may be stably loaded by preventing the leakage of the enzyme even when a stirring reaction is continuously performed after introduction. Furthermore, when a functional group capable of inducing a noncovalent interaction is further introduced into the porous carbon carrier and/or the enzyme utilizing the porous carbon carrier, an interaction between the enzyme and the porous material is enhanced, and thus a larger amount of the enzyme may be loaded in the porous material, and an improved enzyme immobilization and stabilization effect may be exhibited.

In addition, the enzyme may be an enzyme whose amino acids are genetically recombined for the purpose of addition/removal or alteration so as to improve an interaction with the above-described porous carbon carrier, but the present invention is not limited thereto.

Hereinafter, the present invention will be described in detail with reference to embodiments thereof. However, the scope of the present invention is not limited by the embodiments.

Example 1

Manufacture of Formate Dehydrogenase-Immobilized Enzyme-Porous Carbon Composite (FDH-Carbon)

A formate dehydrogenase (FDH) solution (5 mg/mL) prepared in a phosphate buffer solution (100 mM pH 7.0) and 2 mg of porous carbon (mesoporous carbon) powder were mixed in a 2 mL volume, and then the resulting mixture was stirred at 200 rpm for 30 minutes. Through this process, an enzyme-porous carbon composite in which formate dehydrogenase was loaded in the pores of porous carbon was manufactured. Afterward, formate dehydrogenase which had not been loaded in porous carbon was removed, and the resulting composite was washed three times with a phosphate buffer solution and then stored at 4° C.

In this case, the porous carbon had a pore size of 26 nm, a window size of 17 nm, and a pore volume of 1.53 cm$^3$/g.

Comparative Example 1

Manufacture of Formate Dehydrogenase-Immobilized Enzyme-Porous Silica Composite (FDH-Silica)

A FDH solution (5 mg/mL) prepared in a phosphate buffer solution (100 mM pH 7.0) and 2 mg of porous silica (mesoporous silica) powder were mixed in a 2 mL volume, and then the resulting mixture was stirred at 200 rpm for 30 minutes. Through this process, formate dehydrogenase was loaded in the pores of porous silica. Afterward, formate dehydrogenase which had not been loaded in porous silica was removed, and the resulting composite was washed three times with a phosphate buffer solution and then stored at 4° C.

In this case, the porous silica had a pore size of 25 nm, a window size of 18 nm, and a pore volume of 1.90 cm$^3$/g.

Example 2

Manufacture of Glucose Oxidase-Immobilized Enzyme-Porous Carbon Composite (GOx-Carbon)

An enzyme-porous carbon composite was manufactured in the same manner as in Example 1 except that glucose oxidase (GOx) was used as an enzyme.

Comparative Example 2

Manufacture of Glucose Oxidase-Immobilized Enzyme-Porous Silica Composite (GOx-Silica)

An enzyme-porous silica composite was manufactured in the same manner as in Comparative Example 1 except that glucose oxidase (GOx) was used as an enzyme.

Example 3

Manufacture of Carbonic Anhydrase-Immobilized Enzyme-Porous Carbon Composite (CA-Carbon)

An enzyme-porous carbon composite was manufactured in the same manner as in Example 1 except that bovine carbonic anhydrase (bCA) in a phosphate buffer solution (100 mM pH 7.6) was used.

Comparative Example 3

Manufacture of Carbonic Anhydrase-Immobilized Enzyme-Porous Silica Composite (CA-Silica)

An enzyme-porous silica composite was manufactured in the same manner as in Comparative Example 1 except that bovine carbonic anhydrase (bCA) in a phosphate buffer solution (100 mM pH 7.6) was used.

Example 4

Manufacture of Acylase-Immobilized Enzyme-Porous Carbon Composite (AC-Carbon)

An enzyme-porous carbon composite was manufactured in the same manner as in Example 1 except that acylase (AC) was used as an enzyme.

Comparative Example 4

Manufacture of Acylase-Immobilized Enzyme-Porous Silica Composite (AC-Silica)

An enzyme-porous silica composite was manufactured in the same manner as in Comparative Example 1 except that acylase (AC) was used as an enzyme.

Example 5

Manufacture of Vinyl Group-Introduced Glucose Oxidase-Immobilized Enzyme-Porous Carbon Composite (fGOx-Carbon)

An enzyme-porous carbon composite was manufactured in the same manner as in Example 1 except that vinyl group-introduced glucose oxidase was used as an enzyme. In this case, the vinyl group was introduced onto the surface of the enzyme by treating a phosphate buffer solution containing glucose oxidase with acryloyl chloride.

Comparative Example 5

Manufacture of Vinyl Group-Introduced Glucose Oxidase-Immobilized Enzyme-Porous Silica Composite (fGOx-Silica)

An enzyme-porous silica composite was manufactured in the same manner as in Example 5 except that porous silica was used as a carrier.

Example 6

Manufacture of Vinyl Group-Introduced Acylase-Immobilized Enzyme-Porous Carbon Composite (fAC-Carbon)

An enzyme-porous carbon composite was manufactured in the same manner as in Example 1 except that vinyl group-introduced acylase was used as an enzyme. In this case, the vinyl group was introduced onto the surface of the enzyme by treating a phosphate buffer solution containing acylase with acryloyl chloride.

Comparative Example 6

Manufacture of Vinyl Group-Introduced Acylase-Immobilized Enzyme-Porous Silica Composite (fAC-Silica)

An enzyme-porous silica composite was manufactured in the same manner as in Example 6 except that porous silica was used as a carrier.

Comparative Example 7

Free Formate Dehydrogenase (Free FDH)

A FDH solution (5 mg/mL) in a phosphate buffer solution (100 mM pH 7.0) was provided.

Comparative Example 8

Manufacture of Composite in Which Formate Dehydrogenase Crosslinked by Crosslinking Agent (0.01% w/v) was Loaded in Porous Material (FDH-GA_0.01)

A composite in which crosslinked formate dehydrogenase was loaded was manufactured in the same manner as in Example 1 except that glutardialdehyde was added as a crosslinking agent after the addition of the enzyme. In this case, glutardialdehyde was added at a concentration of 0.01% w/v.

Comparative Example 9

Manufacture of Composite in Which Formate Dehydrogenase Crosslinked by Crosslinking Agent (0.1% w/v) was Loaded in Porous Material (FDH-GA_0.1)

A composite in which crosslinked formate dehydrogenase was loaded was manufactured in the same manner as in Example 1 except that glutardialdehyde was added as a crosslinking agent after the addition of the enzyme. In this case, glutardialdehyde was added at a concentration of 0.1% w/v.

Experimental Example 1

Measurement of Enzyme Loading Amount and Release Amount of Enzyme-Porous Carbon Composite Manufactured Using Glucose Oxidase (GOx) and Porous Carbon An enzyme loading amount was determined by quantifying the amount of the enzyme initially introduced for immobilization and the amount of the enzyme released during the washing process via a protein assay and calculating the difference between the initial amount of the enzyme and the amount of the enzyme released during the washing process.

An enzyme release amount was calculated by dispersing a sample in a phosphate buffer solution, continuously quantifying the amount of the enzyme released over time while continuously performing stirring at 200 rpm via a protein assay, and summing the quantified amounts. In this case, the amount of the enzyme released over time was calculated during the process including three washing processes after the enzyme loading, and results thereof are shown in FIG. 6A, FIG. 7A, FIG. 9A, FIG. 10A, and FIG. 11A. Specifically, enzyme release amounts of the enzyme-porous carbon composite of Example 2 in which glucose oxidase and porous carbon were used and the enzyme-porous silica composite of Comparative Example 2 in which glucose oxidase and porous silica were used were compared. As shown in FIG. 7A, Comparative Example 2 showed that all of the loaded glucose oxidase was released within 4 days, whereas Example 2 showed that 65% or more of glucose oxidase remained compared to the initial loading amount when 12 days had elapsed.

Experimental Example 2

Measurement of Enzyme Loading Amount and Release Amount of Enzyme-Porous Carbon Composite Manufactured Using Carbonic Anhydrase (CA) and Porous Carbon A CA-immobilized enzyme-porous carbon composite and a CA-immobilized enzyme-porous silica composite were compared in the same manner as in Experimental Example 1, and results thereof are shown in FIG. 6B and FIG. 7B. As shown in FIG. 7B, Comparative Example 3 showed that all of the loaded CA was released within 1 day, whereas Example 3 showed that 74% or more of CA remained compared to the initial loading amount when 10 days had elapsed.

Experimental Example 3

Measurement of Enzyme Loading Amount and Release Amount of Enzyme-Porous Carbon Composite Manufactured Using Acylase (AC) and Porous Carbon An AC-immobilized enzyme-porous carbon composite and an AC-adsorptively immobilized enzyme-porous silica composite were compared in the same manner as in Experimental Example 1, and results thereof are shown in FIG. 6C, FIG. 7C, FIG. 9B, FIG. 10B, and FIG. 11B. As shown in FIG. 7C, Comparative Example 4 showed that all of the loaded AC was released within 2 days, whereas Example 4 showed that 86% or more of AC remained compared to the initial loading amount when 10 days had elapsed.

Experimental Example 4

Evaluation of Enzyme Activity and Stability of Formate Dehydrogenase-Porous Carbon Composite The initial activity of a formate dehydrogenase-porous carbon composite was measured using an UV-Vis spectrophotometer. More specifically, the formate dehydrogenase-porous carbon composite was added to a mixed solution (containing 200 mM sodium formate, 2 mM NAD+, and a 100 mM sodium phosphate buffer solution), absorbance over time was measured at 340 nm which enables measurement of an NADH amount, and activity was calculated.

The enzyme stability of the formate dehydrogenase-porous carbon composite was evaluated by continuously measuring enzyme activity over time, and results thereof are shown in FIG. 2, FIG. 4, and FIG. 8. In this case, the solution containing the enzyme-porous carbon composite was stored at room temperature while being stirred at 200 rpm.

Experimental Example 5

Evaluation of Enzyme Activity and Stability of Glucose Oxidase-Porous Carbon Composite The enzyme activity of a glucose oxidase-porous carbon composite was measured using an UV-Vis spectrophotometer. More specifically, the glucose oxidase-porous carbon composite was added to a mixed solution containing 3,3',5,5'-tetramethylbenzidine (TMB), glucose, and horseradish peroxidase, absorbance over time was measured at 655 nm, and activity was calculated.

The enzyme stability of the glucose oxidase-porous carbon composite was evaluated by continuously measuring enzyme activity over time, and results thereof are shown in FIG. 3A and FIG. 5A. In this case, the solution containing the enzyme-porous carbon composite was stored at room temperature while being stirred at 200 rpm.

Experimental Example 6

Evaluation of Enzyme Activity and Stability of Carbonic Anhydrase-Porous Carbon Composite The initial activity of a carbonic anhydrase-porous carbon composite was measured using an UV-Vis spectrophotometer. More specifically, the carbonic anhydrase-porous carbon composite was added to a mixed solution in which 60 mM 4-nitrophenyl acetate (4-NA) was dissolved in acetonitrile, and the change in absorbance over time was measured at 348 nm.

The enzyme stability of the carbonic anhydrase-porous carbon composite was evaluated by continuously measuring enzyme activity over time, and results thereof are shown in FIG. 3B and FIG. 5B. In this case, the solution containing the enzyme-porous carbon composite was stored at room temperature while being stirred at 200 rpm.

Experimental Example 7

Evaluation of Enzyme Activity and Stability of Acylase-Porous Carbon Composite

The enzyme activity of an acylase-porous carbon composite was measured using a fluorescence spectrophotometer. More specifically, the change in fluorescence emitted when L-methionine produced by hydrolysis of N-acetyl-L-methionine reacts with o-phthalaldehyde (OPA) was measured.

The enzyme stability of the acylase-porous carbon composite was evaluated by continuously measuring enzyme activity over time, and results thereof are shown in FIG. 3C and FIG. 5C. In this case, the solution containing the enzyme-porous carbon composite was stored at room temperature while being stirred at 200 rpm.

Although the present invention has been described in detail with reference to exemplary embodiments of the present invention, the scope of the present invention is not limited to the exemplary embodiments. It should be understood by those skilled in the art that other exemplary embodiments may be proposed by adding, modifying, and eliminating components and these exemplary embodiments may be included within the scope of the present invention.

The invention claimed is:

1. An enzyme-porous carbon composite comprising:
a porous carbon carrier; and
an enzyme loaded via adsorption in a pore of the porous carbon carrier,
wherein the enzyme is modified by a functional group that induces a hydrophobic interaction between a modified enzyme and a pore surface of the porous carbon carrier.

2. The enzyme-porous carbon composite of claim 1, wherein the enzyme-porous carbon composite exhibits an enzyme release amount of less than 33% compared to before stirring, as measured after being stirred in a buffer solution for 12 days.

3. The enzyme-porous carbon composite of claim 1, wherein the enzyme-porous carbon composite exhibits an enzyme activity of 16% or more compared to before stirring, as measured after being stirred in a buffer solution for 12 days.

4. The enzyme-porous carbon composite of claim 1, wherein the enzyme-porous carbon composite exhibits an enzyme activity of 72% or more compared to before stirring, as measured after being stirred in a buffer solution for 45 days.

5. The enzyme-porous carbon composite of claim 1, wherein the porous carbon carrier further includes a functional group on the pore surface thereof to induce a hydrophobic interaction with the enzyme.

6. The enzyme-porous carbon composite of claim 1, wherein the porous carbon carrier further includes a functional group on the pore surface thereof to induce a hydrophilic interaction with the enzyme.

7. The enzyme-porous carbon composite of claim 5, wherein the functional group of the porous carbon carrier includes one or more hydrophobic interaction-inducing functional groups selected from the group consisting of an alkyl group, a phenyl group, a benzyl group, a vinyl group, and a halo group.

8. The enzyme-porous carbon composite of claim 6, wherein the functional group of the porous carbon carrier includes one or more hydrophilic interaction-inducing functional groups selected from the group consisting of a hydroxy group, a carbonyl group, a halide group, a carboxyl group, a methoxy group, a hydroperoxy group, an amine group, an imine group, an imide group, a nitrile group, a nitro group, a thiol group, a sulfino group, and a phosphate group.

9. The enzyme-porous carbon composite of claim 1, wherein the porous carbon carrier has a pore size of 1 to 5,000 nm.

10. The enzyme-porous carbon composite of claim 1, wherein the enzyme includes one or more enzymes selected from the group consisting of trypsin, chymotrypsin, pepsin, a lipase, glucose oxidase, horseradish peroxidase, tyrosinase, carbonic anhydrase, formaldehyde dehydrogenase, formate dehydrogenase, alcohol dehydrogenase, cholesterol dehydrogenase, acylase, lactonase, a protease, a peroxidase, an aminopeptidase, a phosphatase, a transaminase, serine endopeptidase, cysteine endopeptidase, and a metalloendopeptidase.

11. The enzyme-porous carbon composite of claim 1, wherein the functional group of the enzyme includes at least one of one or more hydrophobic interaction-inducing functional groups selected from the group consisting of an alkyl group, a phenyl group, a benzyl group, a vinyl group, and a halo group.

12. An electrode for a biofuel cell or a biosensor, comprising the enzyme-porous carbon composite according to claim 1.

* * * * *